United States Patent
Kuth

(10) Patent No.: US 7,640,172 B2
(45) Date of Patent: Dec. 29, 2009

(54) DEVICE TO MAKE EXPERT KNOWLEDGE ACCESSIBLE FOR THE OPERATION OF MEDICAL EXAMINATION DEVICES

(75) Inventor: Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1429 days.

(21) Appl. No.: 10/652,272

(22) Filed: Aug. 29, 2003

(65) Prior Publication Data

US 2005/0038311 A1 Feb. 17, 2005

(30) Foreign Application Priority Data

Sep. 11, 2002 (DE) ............................. 102 42 003

(51) Int. Cl.
- A61B 5/00 (2006.01)
- G06Q 10/00 (2006.01)
- G06Q 50/00 (2006.01)
- G06F 19/00 (2006.01)

(52) U.S. Cl. .................. 705/2; 705/3; 600/300
(58) Field of Classification Search ............... None
See application file for complete search history.

(56) References Cited

U.S. PATENT DOCUMENTS

| | | | |
|---|---|---|---|
| 4,835,690 A * | 5/1989 | Gangarosa et al. | 600/410 |
| 5,850,221 A * | 12/1998 | Macrae et al. | 715/853 |
| 6,032,678 A * | 3/2000 | Rottem | 600/437 |
| 6,546,350 B1 * | 4/2003 | Hartmann et al. | 702/119 |
| 6,735,569 B1 * | 5/2004 | Wizig | 705/4 |
| 6,826,546 B1 * | 11/2004 | Shuster | 705/52 |
| 6,915,425 B2 * | 7/2005 | Xu et al. | 713/165 |
| 7,346,858 B1 * | 3/2008 | Berg et al. | 715/853 |

FOREIGN PATENT DOCUMENTS

| | | |
|---|---|---|
| DE | 196 37 219 | 3/1998 |
| DE | 198 50 122 | 10/1999 |

OTHER PUBLICATIONS

FileOpen Systems, "FileOpen Systems Releases FileOpen PDF 2.2", May 26,1999 retrieved from site web.archive.org/web/20011102085258/www.fileopen.com/fopdf22pr.html.*

* cited by examiner

Primary Examiner—C. Luke Gilligan
Assistant Examiner—Eliza Squires
(74) Attorney, Agent, or Firm—Schiff Hardin LLP

(57) ABSTRACT

A device to make expert knowledge available to a user (doctor) of a medical examination device is provided, with a transmission device in order to transcribe at this examination device a handbook procedure of an outside expert in the form of pulse sequences, protocols, parameter sets or the like for the examination device, coordinated with precise medical diagnoses by the inquiring user with an external (if necessary, decentralized) databank which stores settings for a plurality of clinical cases from patient parameters, as well as a computer (expert system) that searches for appropriate suggestions in the databank upon request, and the user submits one or more suggestions according to the result, in that, on a correspondingly expanded user interface of the user examination device, the respective providers are indicated and parallel and offered to be selected.

9 Claims, 1 Drawing Sheet

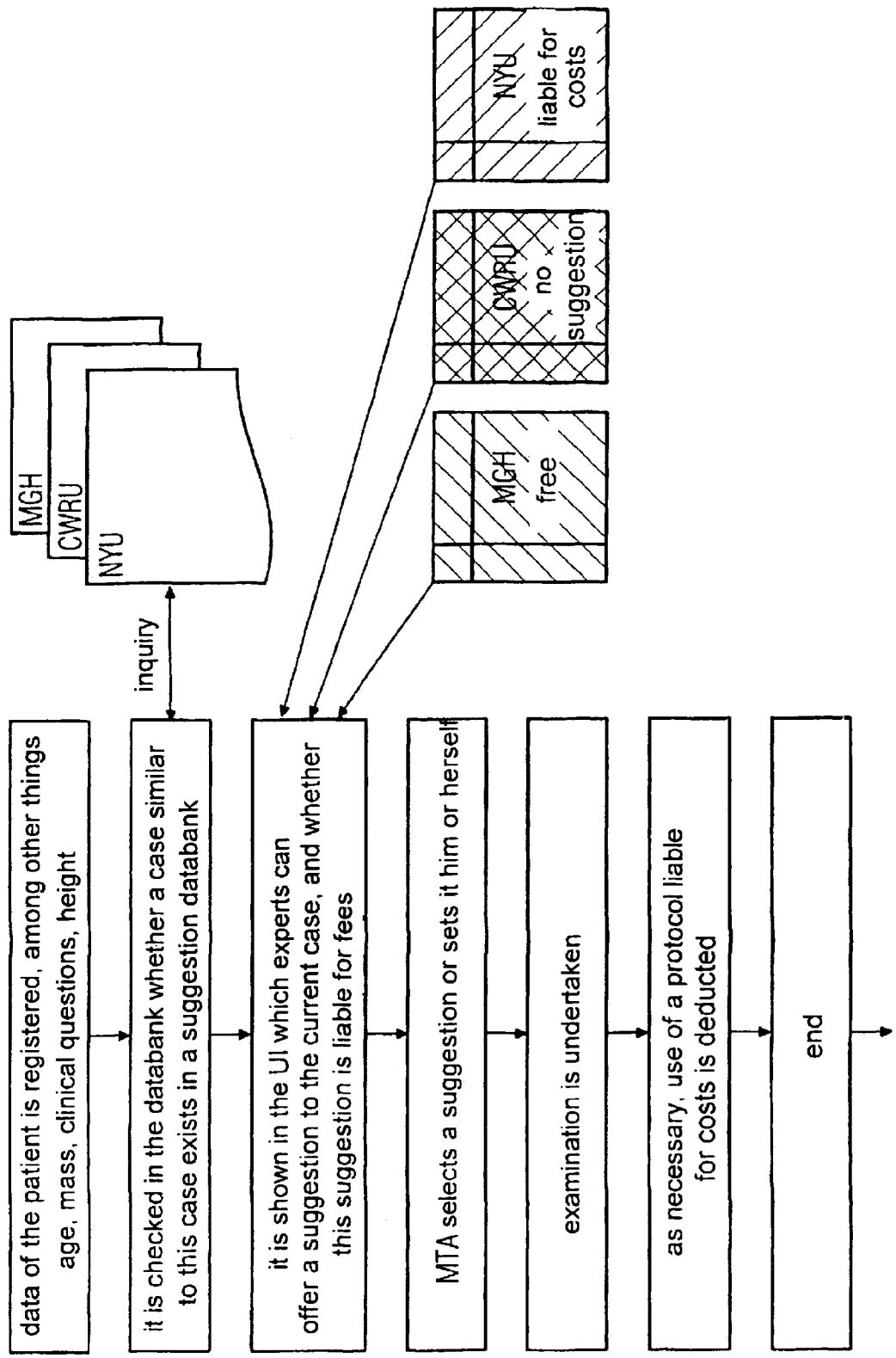

DEVICE TO MAKE EXPERT KNOWLEDGE ACCESSIBLE FOR THE OPERATION OF MEDICAL EXAMINATION DEVICES

BACKGROUND OF THE INVENTION

The invention concerns a device to make expert knowledge available for a user of a medical examination device with a transmission system in order to transcribe at this examination device a handbook procedure of an outside expert in the form of pulse sequences, protocols, parameter sets or the like for the examination device, coordinated with precise medical diagnoses by the inquiring user.

The operation of complex medical examination devices requires a sizable knowledge of the operator if he or she would like to utilize the full capability of the device. Less well-educated users on such devices can profit from the experience of well-educated experts, even when the latter are not directly available for consultation.

This is particularly true for MR scanners which can be adjusted via a plurality of parameters on the basis of particular clinical problems. There are institutes which exercise a substantive function in the definition of clinical protocols.

Additionally, radiologists must abide by "school medicine" in order to avoid malpractice. The problem is that the user, for example, the radiologist in a solo practice, must achieve a simple way of accessing the knowledge of highly specialized clinics or colleagues without having to forego an innate flexibility with regard to the possible settings of the examination device.

A device and a method to detect, process, and evaluate medical measuring data is known from German patent document DE 196 37 219, in which respectively only the measurement heads or similar elements of the examination device are arranged at the location of the user to reduce the device costs for the doctor, while the device components serving for its operation and its evaluation are centrally administered by a provider that is connected to the computer of the doctor.

Apart from the fact that, especially for particularly expensive devices such as MR scanners, no cost savings can be achieved in practice in this manner, since the device components required at the location account for the largest part of the costs, and that the externally located image computer accounts in all cases for at most 10% of the costs of such a device, this known arrangement is not an improved utilization of the device assisting a user, and absolutely not an improved utilization for such devices that already possess all the necessary parts and the necessary image computer as well.

The subject matter of the present invention is not only relevant for the practice of a doctor in single practice that cannot handle the devices, but rather the subject matter of the present invention also makes the expert knowledge available for large practices and clinics, since there is also a need to optimally set the respective devices.

Therefore, an MR scanner is briefly explained below. An MR scanner has approximately 30 setting parameters, including, for example, the echo time, the repetition time, the slice thickness, the slice distance, the slice position in three axes, the number of the averagings per layer, the flip angle, the matrix size in x-direction, y-direction, and z-direction. The optimal setting of such an MR scanner is thus exceedingly complex in light of this plurality of setting parameters, and this setting is often very difficult for the personnel in a clinic to decide. However, given certain intuition of the examiner, respectively different settings must also be undertaken for special x-ray devices and their use that the doctor or the personnel in the clinic can not accomplish when they do not regularly operate such a device.

Published German patent specification DE 198 50 122 A1 discloses a system and method for the configuration and parameterization of a diagnosis device for subjects discussing the overall programming of the diagnosis device. This reference does not address the optimal adaptation of a device to the respective application (thus for example a special setting of a medical examination device according to personal data). This method for configuration and parameterization of a diagnosis device is thus not particularly relevant to the goals of the present invention.

SUMMARY OF THE INVENTION

The invention is therefore based on the object of providing a device of the type cited above such that a particularly simple possible access (also trouble-free for the doctor or his medical technical assistant) to the available expert knowledge is possible for problems of the exact and patient-adjusted setting of a medical examination device.

The present invention provides an external (if need be, decentralized) databank which has in its storage settings for a plurality of clinical cases from patient parameters, as well as a computer (possibly an expert system) that searches for appropriate suggestions by different experts in the databank upon an inquiry. According to the results, the user may submit one or more suggestions or other relevant information. The system may then indicate respective various options that the user can select from a corresponding expanded user interface of the user examination device.

The invention is also based on providing a method for making expert knowledge available to a user of a medical examination device, comprising: providing a handbook procedure by an outside expert, the handbook procedure comprising at least one of pulse sequences, protocols, and parameter sets for the examination device; storing a plurality of handbook procedures in an external decentralized databank in storage area of the databank that includes suggestions for settings for a plurality of clinical cases from patient parameters; entering an inquiry by the user to a computer input related to a current examination; searching, by the computer, appropriate suggestions in the databank based on the inquiry; displaying results of the search on an extended user interface of the examination device in the form of one or more possible suggestions, if available, and concurrently displaying respective providers of the suggestions offered; selecting, by the user on an input to the extended user interface, one of the displayed resulting suggestions; and transcribing, by a transcription device, the handbook procedure with the appertaining selected suggestion for use by the medical device.

DESCRIPTION OF THE DRAWING

The FIGURE is a block diagram illustrating the flow and components of a preferred embodiment of the invention.

DETAILED DESCRIPTION OF THE PREFERRED EMBODIMENTS

According to a preferred embodiment of the invention, after input of known starting parameters by an inquiring user (for example, mass of the patient, age, clinical questions or similar data), the computer searches in the data bank whether one or more suggestions by different experts are available in this case. According to the search results, the computer may offer the operator, e.g., an entire row of suggestions which are thereby indicated and marked in an advantageous manner on the user interface, possibly under an indication of the cost structure.

In an embodiment of the invention, the indicator elements may be highlighted in color according to the cost structure or an ability of a suggestion to be offered or provided.

For example, a row of indicator fields can be arranged on the user interface on which different specialist clinics or specialist experts are indicated, where the name of the clinics or the colleague appears in the operator field. If the indicator field is highlighted in yellow, for example, this shows that no advice is available for current questions at this point.

If, for example, the field is highlighted in green, for example, this means that a suggestion is available and could be selected and transcribed if necessary. A red highlighting of an indicator field may mean that the license account for this provider is expired, and therefore an additional procedure is necessary in order to be able to access the available suggestion.

Altogether, the type of the display and the indication can be fashioned in different ways, but advantageously, the display should make the operation of the system be very simple so that the reply can be surveyed in a single glance, and that in addition it can immediately be recognized as to whether or not the offered solution requires costs to the user. If necessary, a high cost can immediately be inquired afterwards, so that the user that has posed the question in the process of a precise examination of a patient quickly and simply knows whether he can anticipate an external specialist suggestion for the most appropriate setting and parameterization of a medical examination device, and which costs are therefore necessary.

In the vast majority of cases, one does not expect a completely free retrieval of the expert knowledge, one presumes, rather, that the clinics or colleagues will only make their knowledge available as a result of license payments. Thus an embodiment of the invention provides that the transmission device may be coupled with a license billing system that accords a license payment to the experts that develop a handbook procedure or the appropriate clinic, as well as with a disabling device that moreover prevents an expanded usage beyond the stipulated and paid usage.

This disabling device can, for example, be realized in that the handbook procedure contains a start time point and/or an expiration time before or after which it can no longer be used. The handbook procedure may alternately or additionally contains a user limit to a predeterminable number of uses.

Finally, it can also be provided that the handbook procedure contains an identification code that limits the use to one or more target systems and/or specially defined patients or test persons.

Furthermore, a direct debit system that directly collects the license fee with the transmission of the procedure to the user can thereby be advantageously provided.

It has proven to be particularly beneficial to encrypt the handbook procedure as a data set, and to directly import it into the examination device in order to control the parameter settings and examination sequences.

Referring now to the FIGURE illustrating a preferred embodiment, the doctor or the medical technical assistant initially registers the data of the patient, including the age, weight, height, and various clinical questions, and gives this data as an inquiry to a computer with an external, (if necessary, decentralized) databank distributed via the internet, in which are stored proposals by a plurality of specialized clinics or experts for the handbook procedure of the medical examination device of the user.

The data bank is queried as to whether or not a suggestion exists for this case or a very similar case—the plurality of the experts and specialized clinics in the external databank in the attached diagram being denoted by the three pages with the abbreviations for the names of these clinics on them.

It is shown on the user interface of the provider which of the experts can offer advice to the current case, and whether this is liable for charges. In the attached drawing, a case is shown in which the one expert can offer no suggestion for the question, one of the vendors (MGH) has a suggestion that can be accepted for free, and another vendor likewise has a solution suggestion that is, however, liable for fees. The designations "free", "liable for fees", "no suggestion" do not need to be shown as text as in the drawing, but rather it can, for example, be provided by other methods, e.g., that the case "no suggestion" is indicated by a yellow highlighting of the corresponding indicator field, the free suggestions are highlighted white, fee-liable suggestions green, and fee-liable suggestions from specialty clinics or colleagues with whom the license account of the user has expired are red.

The doctor or the MTA may select a suggestion or may set the parameters herself, whereupon the examination is implemented. Parallel to this, the use of a fee-liable protocol may be implemented, preferably in the manner that the corresponding license fee is debited directly from the account of the user with the transmission of the handbook procedure from the expert to the examination device of the user.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A method for making expert knowledge available to an inquiring user of a medical examination device to provide at least one parameter set procedure of an outside expert comprising a parameter set for said medical examination device coordinated with an inquiry based on patient data for a patient by said inquiring user, comprising the steps of:

providing said user with a computer and user interface display which is connected by a transmission system to access an external decentralized data bank, said data bank having stored therein a plurality of suggestions for parameter sets for said medical examination device;

said user using said computer to request from said external decentralized data bank at least one suggestion for a parameter set for the user's medical examination device for said inquiry based on patient data sent by the user to said data bank;

said computer receiving from said external decentralized data bank fee information indicating whether a fee is required and an amount of said fee for use of at least one suggested parameter set in response to said user inquiry, and in response to accepting the fee, said computer receiving said at least one suggested parameter set and displaying said at least one parameter set on said display, and the accepted fee being debited from an account of said user; and said user using said at least one parameter set to set said medical examination device for operation of said medical examination device on the patient for whom said inquiry was made.

2. A method of claim 1 wherein in addition to said parameter set a pulse sequence for said medical examination device is also provided.

3. A method of claim 1 wherein in addition to said parameter set at least one protocol is provided for adjusting said medical examination device.

4. A method of claim 1 wherein said at least procedure comprises a handbook procedure by said outside expert.

5. A method of claim 1 wherein said data bank indicates whether or not there is a cost associated with supplying said parameter set to said user.

6. A method of claim 1 wherein on the display for said computer it is indicated to said user whether a cost is associated with the suggested parameter set by color coding.

7. A method of claim 1 wherein a disabling device prevents further usage of said external data bank via said computer if a paid usage fee would be exceeded by receiving said parameter set for which a charge is being made.

8. A method of claim 1 wherein the medical examination device comprises an MR machine.

9. A system for making expert knowledge available to an inquiring user of a medical examination device by providing at least one parameter set procedure of an outside expert for said medical examination device coordinated with an inquiry based on patient data for a patient by said inquiring user, comprising:

a computer for said user and a user interface display which is connected by a transmission system to access an external decentralized data bank, said data bank having stored therein a plurality of suggestions for parameter sets for said medical examination device;

said computer requesting from said external decentralized data bank for said inquiry based on patient data from said user at least one suggestion for a parameter set for the user's medical examination device; and said computer receiving from said external decentralized data bank fee information indicating whether a fee is required and an amount of said fee for use of at least one suggested parameter set in response to said user inquiry, and in response to accepting the fee, said computer receiving said at least one suggested parameter set, and said display displaying said at least one parameter set, and said computer indicating to said decentralized data bank acceptance of the fee and the accepted fee is debited from an account of said user, said user using said at least one parameter set to set said medical examination device for operation of said medical examination device on the patient for whom said inquiry was made.

* * * * *